United States Patent [19]

Miller et al.

[11] Patent Number: 5,430,218
[45] Date of Patent: Jul. 4, 1995

[54] DEHYDROGENATION USING DEHYDROGENATION CATALYST AND POLYMER-POROUS SOLID COMPOSITE MEMBRANE

[75] Inventors: Stephen J. Miller, San Francisco, Calif.; Mary E. Rezac; William J. Koros, both of Austin, Tex.

[73] Assignees: Chevron U.S.A. Inc., San Francisco, Calif.; Board of Regents, University of Texas System, Austin, Tex.

[21] Appl. No.: 113,459

[22] Filed: Aug. 27, 1993

[51] Int. Cl.⁶ ............................................. C07C 5/333
[52] U.S. Cl. ................................. 585/654; 585/660
[58] Field of Search ............................. 585/654, 660

[56] References Cited

U.S. PATENT DOCUMENTS

| | | | |
|---|---|---|---|
| Re. 29,948 | 3/1979 | Swyer et al. | 208/110 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 4,016,245 | 4/1977 | Plank et al. | 423/328 |
| 4,046,859 | 9/1977 | Plank et al. | 423/328 |
| 4,061,724 | 12/1977 | Grose et al. | 423/335 |
| 4,073,865 | 2/1978 | Flanigen et al. | 423/339 |
| 4,076,842 | 2/1978 | Plank et al. | 423/328 |
| 4,124,649 | 11/1978 | Rausch | 260/665 |
| 4,238,318 | 12/1980 | Kouwenhoven et al. | 208/120 |
| 4,268,420 | 5/1981 | Klotz | 252/432 |
| 4,269,813 | 5/1981 | Klotz | 423/277 |
| 4,299,808 | 11/1981 | Klotz | 423/331 |
| 4,327,236 | 4/1982 | Klotz | 585/481 |
| 4,397,827 | 8/1983 | Chu | 423/326 |
| 4,401,555 | 8/1983 | Miller | 208/111 |
| 4,438,288 | 3/1984 | Imai et al. | 585/379 |
| 4,481,177 | 11/1984 | Valyocsik | 423/329 |
| 4,483,835 | 11/1984 | Zones | 423/277 |
| 4,556,477 | 12/1985 | Dwyer | 208/111 |
| 4,636,483 | 1/1987 | Kjell et al. | 502/61 |
| 4,665,267 | 5/1987 | Barri | 585/660 |
| 4,795,732 | 1/1989 | Barri | 502/223 |
| 4,835,336 | 5/1989 | McCullen | 585/419 |
| 4,859,442 | 8/1989 | Zones et al. | 423/277 |
| 4,929,792 | 5/1990 | Dessau | 585/660 |
| 4,962,250 | 10/1990 | Dessau et al. | 585/660 |
| 5,052,561 | 10/1991 | Miller et al. | 208/137 |
| 5,053,373 | 10/1991 | Zones | 502/64 |
| 5,200,375 | 4/1993 | Dessau | 585/660 |
| 5,227,141 | 7/1993 | Kim et al. | 585/660 |

FOREIGN PATENT DOCUMENTS 0102716  3/1984  European Pat. Off. .

OTHER PUBLICATIONS

Journal of Catalysis 58, 114–130 (1979) "Reactions on ZSM-5-Type Zeolite Catalysts"; J. R. Anderson et al.
Elsevier Science Pub. B. V., Amsterdam Applied Catalysis, 49 (1989) 1–25 "Catalysis with Permselective Inorganic Membranes"; J. N. Armor.
Nature vol. 280 (1979) 664–665; "Silicalite-2, A Silica Analogue of the Aluminosilicate Zeolite ZSM-11"; D. M. Bibby et al.
Nature vol. 271 512–516 (1978) "Silicalite, A New Hydrophobic Crystalline Silica Molecular Sieve" E. M. Flanigen et al.
Book TP/156/C35/S27 "Processing of Petroleum and Hydrocarbons—9.11 Dehydrogenation—9.11.1 Butadiene from Butane and Butene" 268–270.
Gas Transport Properties of Polysulphones 341–342 (1991) "Condensation of the Research" J. S. McHattie et al.
Polymer, 1991 vol. 32, No. 14 "Gas Transport of Properties of Polysulphones: 2. Effect of Bisphenol Connector Groups" 2618–2625; J. S. McHattie et al.

(List continued on next page.)

Primary Examiner—Asok Pal
Attorney, Agent, or Firm—W. Keith Turner; Richard J. Sheridan

[57] ABSTRACT

Light paraffinic hydrocarbons are catalytically dehydrogenated using a dehydrogenation catalyst and a polymer-porous solid composite membrane capable of separating hydrogen from the effluent of the dehydrogenation reaction. The polymer-porous solid composite membrane may be, e.g., a porous ceramic material coated with a fluorinated dianhydride-diamine, a fluorinated polycarbonate or fluorinated polysulfone.

10 Claims, 2 Drawing Sheets

OTHER PUBLICATIONS

The Univ. of Texas–Austin, Separations Research Program, Publication No. K-90-9 "Gas Permeation and Sorption in a Series of Aromatic Polycarbonates" (1990) M. W. Hellums, B. S., M. S. ChE.

The Univ. of Texas–Austin, Separations Research Program, Publication No. K-88-3 "Gas Sorption and Permeation in a Series of Aromatic Polyimides" (1988) Tae-Han Kim.

WO91/13130—Miller, Stephen J. "Dehydrocyclization or Catalytic Reforming Using Sulfur Tolerant Zeolite Catalyst"—Sep. 5, 1991.

Journal of Applied Polymer Science, vol. 46 1927–1938 (1992)—M. E. Rezac et al. "Preparation of Polymer–Ceramic Composite Membranes with Thin Defect-Free Separating Layers"—pp. 1927–1938.

Ind. Eng. Chem. Fundam. 1981. 10, 97–99–T. Kameyama—"Possibility for Effective Production of Hydrogen from Hydrogen Sulfide by means of a Porous Vycor Glass Membrane".

1992 The Chemical Society of Japan; Bull. Chem. Soc. Jpn, 55, 2760–2764 (1982) vol. 55, No. 9; O. Shinji et al. Hydrogen Energy, vo. 9 No. 10 pp. 835–839, 1984—N. Ito et al—"Enhanced Catalytic Decomposition of HI by Using A Microporous Membrane".

Ind. Eng. ChemRes. 1988, 27, 1136–1142; Y–M Sun et al "Catalytic Membrane for Simultaneous Chemical Reaction and Separation Applied to a Dehydrogenation Reaction".

Chemical Engineering Science, vol. 45, No. 8 pp. 2423–2429, 1990—A. M. Champagnie et al. "A High Temperature Catalytic Membrane Reactor For Ethane Dehydrogenation".

Ind. Eng. Chem. Res. 1991, 30, 614–616; T. Okubo—'‘Equilibrium Shift of Dehydrogenation at Short Space-Time wiht Hollow Fiber Ceramic Membrane".

Chemtracts–Macromolecular Chemistry 2:341–343 (1991)—J. S. McHattie et al. "Gass Transport Properties of Polysulphones: 1. Role of Symmetry of Methyl Group Placement on Bisphenol Rings".

The Univ. of Texas–Austin, "Gas Transport Properties of Polysulfone Membrane Materials"—Dissertation—pp. 1–316, May 1992, C. L. Aitken, B. S, M. S.

Figure 1: Effect of Temperature on Gas Transport Rates in Polyimide-Ceramic Composite Membranes Figure 2: Effect of Temperature on the Separation Ability of Polyimide-Ceramic Composite Membrane Figure 3: Stability of Butane Dehydrogenation Catalyst as a Function of Run Time. Reactor Temperature = 900 °F, Pressure = 1.10 psig, LHSV = 5 per bed

DEHYDROGENATION USING DEHYDROGENATION CATALYST AND POLYMER-POROUS SOLID COMPOSITE MEMBRANE

BACKGROUND OF THE INVENTION

The present invention relates to catalytic dehydrogenation of paraffins using a catalyst which preferably contains a crystalline zeolite, and a thermally stable polymer-porous solid membrane capable of separating hydrogen from the dehydrogenation reaction effluent. Dehydrogenation is a well-known reaction wherein paraffins are converted to olefins With $C_6+$ hydrocarbons dehydrogenation is generally accompanied by dehydrocyclization and aromatization reactions. With $C_2$-$C_5$ alkanes, dehydrogenation reactions follow different reaction pathways, depending on molecular type. Reaction equilibria reflect these differences in reaction pathways. It is important, therefore, to provide a catalyst and process conditions specifically for the dehydrogenation of a light paraffinic hydrocarbon feed.

The overall objective of this invention is to use thermally stable polymer-porous solid composite membranes to improve the conversion achievable at a given temperature in the equilibrium-limited catalytic dehydrogenation of paraffins.

The catalysts of the present invention are dehydrogenation catalysts. Preferably the catalyst comprises a zeolite, and more preferably the zeolite contains a specific quantity of alkali and/or alkaline earth components. Dehydrogenation catalysts containing alkali or alkaline earth components are known. In C. N. Satterfield, *Heterogeneous Catalysis in Practice*, New York: McGraw-Hill Book Company, 1980, p. 269, an $Fe_2O_3$—$Cr_2O_3$—$K_2CO_3$ butene dehydrogenation catalyst is described, in which the potassium component helps to maintain catalyst activity by promoting the reaction between steam in the feed and coke deposited on the catalyst.

U.S. Pat. No. 4,124,649 to Rausch discloses a porous, non-acidic carrier material containing a platinum or palladium component, a rhodium component, and a tin component for use in dehydrogenation. The non-acidic carrier material contains about 0.1 to about 5 wt % of an alkali metal or alkaline earth metal. Lithium and potassium are preferred. It is taught that the function of the alkali/alkaline earth component is to neutralize any of the acidic material which may have been used in the preparation of the dehydrogenation catalyst.

U.S. Pat. No. 4,438,288 to Imai and Hung describes a dehydrogenation catalyst containing a platinum group component, a porous support material, and an excess of an alkali or alkaline earth component relative to the platinum group component. This catalyst is taught as being particularly useful for dehydrogenating paraffins having from 2 to 5 or more carbon atoms to the corresponding mono-olefins or for dehydrogenating mono-olefins having 3 to 5 or more carbon atoms to the corresponding di-olefins.

Crystalline molecular sieve zeolites have also been disclosed for dehydrogenation of paraffinic hydrocarbons. As with the art cited above, which teaches use of a non-crystalline dehydrogenation catalyst, the acidity of the zeolitic-containing dehydrogenation catalysts is an important variable. For example, U.S. Pat. No. 4,665,267 and U.S. Pat. No. 4,795,732, both to Barri teach using a catalyst having a silicalite support and containing a platinum group metal for the dehydrogenation of $C_2$ to $C_{10}$ paraffins. The catalyst of Barri is substantially free of alkali and alkaline earth metals.

U.S. Pat. No. 4,401,555 to Miller is directed to olefin production from paraffins using silicalite having a low sodium content. The silicalite used in the '555 process contains less than 0.1 wt % sodium and is composited in a matrix which is substantially free of cracking activity. Also, the composite has no hydrogenation component. According to the '555 process, the paraffinic feed may be hydrotreated to reduce sulfur levels to less than 100 ppm organic sulfur.

An intermediate pore size crystalline silicate having a high silica to alumina ratio, a relatively low alkali content, and a small crystallite size is taught as a sulfur tolerant reforming or dehydrocyclization catalyst in International Patent Application WO91/13130.

Other non-acidic catalysts have been proposed for dehydrogenation of paraffins. In U.S. Pat. No. 4,962,250, a non-acidic MCM-22 zeolite, in combination with a Group VIII metal species, is taught for dehydrogenation of $C_2$-$C_{12}$ aliphatic hydrocarbons. In order to be non-acidic, the '250 reference teaches that the finished catalyst should contain cation equivalents of Group IA and/or IIA cations equal to or greater than the framework aluminum content.

In U.S. Pat. No. 4,929,792 to Dessau, a zeolite Beta in non-acidic form is disclosed for dehydrogenation of a $C_2$-$C_{12}$ paraffin-containing feed. To render the Beta zeolite non-acidic, '792 teaches titrating the zeolite with Group IA or IIA in ion-exchangeable form until a Ph of greater than 7 is achieved.

Dehydrogenation processes in which hydrogen is separated from the dehydrogenation reaction zone are known. Processes available to the art include those for separating hydrogen from liquid and/or gaseous hydrocarbon streams. Such processes include distillation, adsorption, absorption, extraction and permeation through a semipermeable membrane. For example, J. N. Armor, *Applied Catalysis*, 49, 1 (89) describes separation processes for recovering a purified hydrogen stream from hydrogen/hydrocarbon mixtures using a semipermeable membrane. Examples of membranes which have been used include metal or metal alloy of high permeability to hydrogen (e.g., Pd, Pd/Ag), either alone as a thin foil or as a thin film on a support also permeable to hydrogen (e.g., porous ceramic, glass). Non-metallic inorganic membranes and polymer membranes are also known to the art.

Polymer-ceramic composite membranes are also known. M. E. Rezac and W. J. Koros, *Journal of Applied Polymer Science*, 46, pp. 1927–1938 (1992) disclose the preparation of polymer-ceramic composite membranes comprising essentially defect-free, thin (<1 82 m) dense-skinned organic-inorganic composite membranes. These membranes are useful for gas separations.

The polymers used by Rezac and Koros for the production of the dense organic separating layer of their composites were (1) a fluorine-containing dianhydride-diamine polymer, 4,4'[2,2,2-trifluoro-1-(trifluoromethyl)ethylidene]bis-1,3-isobenzofuran-dione, isopropylidene-dianiline (6FDA-IPDA); (2) bisphenol-A polycarbonate (PC); (3) tetramethylhexafluorobisphenol-A polycarbonate (TMHFPC); (5) tetramethylhexafluoropolysulfone (TMHFPSF) and (6) 4,4'-[2,2,2-trifluoro-1-(trifluoromethyl)ethylidene]bis-1,3-isobenzofuran-dione, methylene-dianiline (6FDA-MDA).

Thus, while catalytic dehydrogenation processes are known, including those which utilize a semipermeable membrane to separate hydrogen, there still exists a need for more efficient processes which provide higher conversion of paraffin to olefin. The present invention provides such a process in which conversions of paraffin to olefin are significantly higher than with conventional systems while at the same time operating several hundred degrees Fahrenheit lower than do the conventional systems which typically operate at about 450° C. (842° F.) to about 700° C. (1292° F.).

SUMMARY OF THE INVENTION

The present invention provides a process for dehydrogenating a light paraffin hydrocarbon feed, said process comprising:

A. contacting said feed under catalytic dehydrogenation conditions with a dehydrogenation catalyst;

B. contacting the effluent from the dehydrogenation reaction of step A with a thermally stable polymer-porous solid composite membrane capable of separating hydrogen from said effluent, thereby separating said effluent into components comprising (1) hydrogen and (2) a mixture comprising paraffin and olefin.

In a preferred embodiment, the mixture of paraffin and olefin is contacted with additional dehydrogenation catalyst, under catalytic dehydrogenation conditions, to dehydrogenate at least a portion the paraffins in said mixture.

The present invention also provides a process for dehydrogenating a light paraffinic hydrocarbon stream using a catalyst with high selectivity and low deactivation rate. More specifically, a process is provided for dehydrogenating a light paraffinic hydrocarbon feed which process comprises:

A. contacting the feed under catalytic dehydrogenation conditions with a catalyst comprising:
  (a) a noble metal;
  (b) an intermediate pore size zeolite having a silica to alumina ratio of at least about 30, preferably at least about 200; and more preferably at least about 500; and
  (c) an alkali content wherein the alkali to aluminum ratio in the zeolite is between about 1 and about 5, and preferably between about 1 and about 3, on a molar basis; and B. contacting the effluent from step A with a polymer-porous solid composite membrane capable of separating hydrogen from said effluent, thereby separating said effluent into components comprising (1) hydrogen and (2) a mixture comprising paraffin and olefin.

In a preferred embodiment, the mixture of paraffin and olefin is contacted with additional dehydrogenation catalyst, under catalytic dehydrogenation conditions, to dehydrogenate at least a portion of the paraffins in said mixture.

Among other factors, the present invention is based on the discovery that high conversion of paraffin to olefin is achievable in a dehydrogenation process which utilizes a polymer-porous solid composite membrane to separate hydrogen from the effluent from the dehydrogenation reaction. It is particularly surprising that these high conversions can be achieved even at temperatures hundreds of degrees Fahrenheit lower than the temperature commonly used in conventional dehydrogenation processes.

The present invention is also based on the finding that when the process of the present invention utilizes a dehydrogenation catalyst comprising a noble metal and an intermediate pore size zeolite having a silica to alumina ratio of at least about 30 and said catalyst is treated with specific amount of an alkali and/or alkaline earth component, a surprisingly low deactivation or fouling rate is achieved and a surprisingly high selectivity and activity for dehydrogenation can be attained. It has also been found that such low fouling rates are achieved even after sulfur breakthrough or other periodic exposure of dehydrogenation catalyst to sulfur. Fouling or deactivation rate is the rate at which the dehydrogenation zone reaction temperature needs to be raised per unit time, e.g., °F. per hour, in order to maintain a given feed conversion.

It has further been found that it is advantageous to sulfide said dehydrogenation catalyst. The sulfiding can be done by known presulfiding techniques, for example, by passing a gas stream containing hydrogen sulfide over said catalyst prior to commencing the dehydrogenation run, or the sulfiding of the catalyst can be carried out through the sulfur in the feed to the process. It has been found that, in catalytic dehydrogenation, the combination of a specific alkali level in the intermediate pore size zeolite of high silica to alumina ratio and sulfiding of the catalyst allows the achievement of surprisingly good olefin yields, high selectivity to olefins and low fouling rates even after exposure to sulfur.

It has also been found that, when the aforementioned intermediate pore size catalyst is used in the process of the present invention, it is advantageous to use small crystallite size intermediate pore size zeolite of high silica to alumina ratio. Small crystallite size for this component of the catalyst is discussed in more detail in U.S. Pat. No. 5,052,561, issued Oct. 1, 1991, and titled "A Crystalline Silicate Catalyst and a Reforming Process Using the Catalyst". The disclosure of U.S. Pat. No. 5,052,561 is incorporated herein by reference, particularly its disclosure with regard to small crystallite size intermediate pore size zeolite and methods of making such crystallites. Preferred small crystallite sizes for the present invention are less than 10 microns, more preferably less than 5 microns, still more preferably less than 2 microns, and especially preferred less than a micron. The size is on a basis of the largest dimension of the crystallites. Preferred shapes for the crystallites are approximately spherical. When a crystallite size is specified, preferably at least 70 wt % of the crystallites are within the specified range, more preferably at least 80 wt % and most preferably at least 90 wt %.

Thus, according to a preferred embodiment of the present invention, the catalyst used in the dehydrogenation process comprises an intermediate pore size zeolite of small crystallite size and having a high silica to alumina ratio with a specific alkali content. According to a particularly preferred embodiment, the catalyst is presulfided or is sulfided during dehydrogenation operations. Among other reasons, this catalyst is preferred because it is highly stable in the absence of hydrogen, thus allowing the removal of hydrogen from the dehydrogenation reaction effluent by the polymer-ceramic composite membrane without adversely affecting the catalyst. Ordinary catalysts would require the addition of hydrogen to maintain their stability.

DETAILED DESCRIPTION OF PREFERRED EMBODIMENTS

The present invention uses thermally stable polymer-porous solid composite membranes to improve the efficiency of energy intensive dehydrogenation reaction processes. To illustrate this technique, the present invention will be exemplified by dehydrogenation of butane to butene, viz., (1)

Previous efforts to achieve high temperature membrane operation have sacrificed membrane performance for thermal stability by relying upon inorganic microporous ceramics and dense metals as membranes. Ceramics and metals separate gases using vastly different mechanisms. Porous ceramics typically separate gases via the Knudsen diffusion mechanism. In this regime, the pore diameter of the membrane is smaller than the mean free path of the gas molecules. Thus, the gases bounce into the walls more often than they bounce into each other. Kinetic energy is lost in these collisions, and the as molecules pass through the porous material at a rate inversely proportional to their mass. Therefore, the maximum separation selectivity which is possible is controlled by the mass of the species. For the separation of hydrogen from butane, the separate selectivity is 5.8. This is nearly two orders of magnitude lower than that possible in an appropriately chosen glassy polymer.

Conversely, molecular hydrogen can pass through the lattice of certain metals, especially palladium. In this process, hydrogen is adsorbed on the surface of the metal and dissociated, passes through the metal matrix and the molecule is reformed at the low pressure side of the metal. The driving force for this transport is a difference in the partial pressures of hydrogen at each face of the metal. All other gases are too large to pass through the metal matrix. Thus, near-perfect separation is possible through the use of metals. However, several limitations have been observed in the use of palladium for the separation of hydrogen from as mixtures. First, hydrogen embrittlement has been reported in these metals. This can result in the formation of cracks in the metal if it is subject to temperature cycles. Any cracks or pinholes in the metal matrix will result in a dramatic loss in the separation ability of the membrane. Second, palladium is known to react with sulfur compounds to form palladium sulfide which is capable of performing the hydrogen dissociation reaction and therefore, renders the membrane useless. Finally, the technology to form this rather expensive material into a very thin, defect-free form is not currently available. Without this ability, the membrane area required even for simple separations may be prohibitive.

Previous attempts have been made to produce membrane reactors. See, for example, T. Kameyama et al., "Possibility of Effective Production of Hydrogen From Hydrogen Sulfide by Means of a Porous Vycor Glass Membrane," *Ind. Eng. Chem. Fundam.*, (20), pp. 97–99 (1981); O. Shinji et al., "The Dehydrogenation of Cyclohexane by the Use of a Porous-Glass Reactor," *Bull. Chem. Soc. Jpn.*, (55), pp. 2760–2764 (1982); N. Itoh et al., "Enhanced Catalytic Decomposition of HI by Using a Microporous Membrane," *Int. J. Hydrogen Energy*, (9), pp. 835–839 (1984); Y. Sun et al., "Catalytic Membrane for Simultaneous Chemical Reaction and Separation Applied to Dehydrogenation Reaction," *Ind. Eng. Chem. Res.*, (27), pp. 1136–1142 (1988); A Champagnie et al., "A High temperature Catalytic Membrane Reactor For Ethane Dehydrogenation," *Chemical Engineering Science*, (45), pp. 2423–2429 (1990); and T. Okubo et al., "Equilibrium Shift of Dehydrogenation at Short Space-Time with Hollow Fiber Ceramic Membrane," *Ind Eng. Chem. Res.*, (30), pp. 614–616 (1991).

In some previous attempts to use membranes to affect the degree of conversion in an equilibrium-limited reaction, the catalyst was either contained integrally within a microporous tube or deposited in the pores of the microporous ceramic membrane substrate, and the relatively small differences in Knudsen diffusivities of the components were the only source of selectivity for shifting the reaction equilibrium. On the other hand, the present invention involves decoupling the separation and reaction processes to provide for maximum flexibility and control. Further, the present invention allows for retrofitting existing reactor systems at a fraction of the cost of constructing new membrane-reactors. In realistic industrial dehydrogenation operations where coke formation on the catalyst requires regeneration, such a decoupling of the membrane and reactor is desirable for successful implementation.

The process of the present invention uses polymer-porous solid composite membranes. These membranes have selectivities which are markedly higher than the porous ceramic materials, while their gas transport rates are higher than those of the dense metal materials. The porous solid substrate in these polymer-porous solid composites provides mechanical strength and stability while introducing essentially no resistance to gas flow. The thin polymer layer provides the separation media.

Polymer-Porous Solid Composite Membrane Formation

Polymer-porous solid composite membranes can be prepared using as the solid substrate a porous solid. As used herein, the term "porous solid" refers to solid materials which have pores which are smaller in diameter than the solvated diameter of the polymer used to make the polymer-porous solid composite membranes. Typically, that only that they are not so small that they inhibit the passage of hydrogen through the composite. The porous solid must also be stable at the temperatures at which the hydrogen removal is carrier out. It must also be resistant to the solvent used to apply the polymer layer to the porous solid, i.e., the porous solid does not dissolve or swell when contacted with the solvent. Finally, the porous solid should have adequate mechanical strength to withstand handling and the pressure differentials encountered in the hydrogen separation zone.

Preferred porous solid materials are commercially available ceramic filters. These ceramic filters, produced by Anotech Separations under the designation Anodisc ®, are γ-Al$_2$O$_3$ membranes which are synthe- sized by an anodic oxidation process. These ceramic filters have an average surface pore diameter of 200 Å and an average surface porosity of approximately 50%. In some cases, these ceramic filters have 2000 Å capillaries which branch into 200 Å pores at the surfaces. Thus, these materials have very limited resistance to gas flow, and with proper support have sufficient structural strength to withstand pressure differentials of over 200 psig. The filters typically are about 60 μm thick and can be used as received from the manufacturer without further treatment.

Polymers are chosen based on the combination of gas transport rates and selectivity, availability and maximum use temperature. The polymers used for production of the polymer-porous solid composite membranes, useful in the present invention, were all high molecular weight, semi-rigid materials. These included two fluorine-containing polyimides, a substituted fluorine-containing polycarbonate and a fluorine-containing fluorine-containing polyimides, a substituted fluorine-containing polycarbonate and a fluorine-containing polysulfone. It is believed that aromatic polyamides, including fluorinated aromatic polyamides are also useful.

The polyimides were the fluorine-containing materials shown below:

4,4'-[2,2,2-trifluoro-1-(trifluoromethyl)
ethylidene]bis-1,3-isobenzofuran-dione,
isopropylideneaniline
(6FDA - IPDA)

4,4'-[2,2,2-trifluoro-1-(trifluoromethyl)
ethylidene]bis-1,3-isobenzofuran-dione,
methyleneaniline
(6FDA - MDA)

The fluorine-containing polyimides can be synthesized by known techniques. See, for example, T. H. Kim, Ph.D Dissertation, The University of Texas at Austin (1987).

The substituted fluorine-containing polycarbonate was tetramethylhexafluorobishphenol-A polycarbonate (TMHFPC) which has the structure:

Tetramethylhexafluoro
Bisphenol - A Polycarbonate (TMHFPC)

The substituted fluorine-containing polycarbonates may also be prepared by known methods. See, for example, M. W. Hellums, Ph.D. Dissertation, The University of Texas at Austin (1990).

The fluorine-containing polysulfone was tetramethylhexafluoropolysulfone (TMHFPSF) which has the structure:

Tetramethylhexafluoropolysulfone (TMHFPSF)

The fluorine-containing polysulfones can be made using known methods. See, for example, J. S. McHattie, W. J. Koros and D. R. Paul, "Gas transport properties of polysulfones. Part I: Role of symmetry of methyl group placement on bisphenol rings", *Polymer* 32, 840 (1991); J. S. McHattie, W. J. Koros and D. R. Paul, "Gas transport properties of polysulfones. Part II: Effect of bisphenol connector groups", *Polymer*, 32, 2618 (1991); and C. Aitken, Ph.D Dissertation, The University of Texas at Austin (1992).

Some of the physical properties of these polymers are shown in Table 1 below. The glass transition temperature, $T_g$, of the polymers can be regarded as the upper temperature for use of the polymer in gas separation membranes. Above this temperature, the polymer losses mechanical strength and its ability to separate gas molecules is dramatically reduced.

TABLE 1

| Physical Properties of Polymers | | |
|---|---|---|
| Polymer | Density (gm/cc) | $T_g$ (°C.) |
| 6FDA-IPDA | 1.352 | 310 |
| 6FDA-MDA | 1.400 | 304 |
| TMHFPC | 1.286 | 208 |
| TMHFPSF | 1.286 | 243 |

The polymer-porous solid composite membranes of this invention can be produced by the deposition of a thin polymer layer on a microporous ceramic support as described in M. E. Rezac and W. J. Koros, *Journal of Applied Polymer Science*, (46), pp. 1927–1938 (1992), which is hereby incorporated by reference in its entirety. Dilute solutions of 0.05 to 1.0 wt % of polymer in methylene chloride are prepared and filtered. The porous solid, e.g., ceramic filter is placed on a clean glass plate and a measured volume of the polymer-containing solution applied directly to the solid. The nascent membrane is maintained in a solvent saturated environment for a minimum of one hour and then further dried in air for approximately six hours. Finally, the membranes are dried under vacuum at 100° C. for a minimum of one hour to ensure the removal of all solvent.

Since the productivity of the polymer layer is inversely proportion to the layer's thickness, it is preferable to apply as thin a polymer layer as possible to the porous solid. The layer must not, however, become so thin that voids or other defects in its integrity begin to appear. Also, since different polymers can have different gas flux properties, it may be desirable to deposit a thinner layer for some polymers than for others. Likewise, some polymers may be able to tolerate a thicker layer and still maintain useful gas flux properties. With these factors in mind, the polymer layer will generally be from about 1 μm to about 5 μm thick, preferably about 1 μm or less.

As standard, test penetrants, the flux of nitrogen, oxygen and helium were measured for the composites of this invention made from ceramic filters having 200 Å pores. Results are presented in Table 2 and 3. The majority of the work was conducted using a preferred polyimide, 6FDA-IPDA. This material was preferred because of its high glass transition temperature and hence good mechanical stability at elevated temperature. Table 2 presents the gas flux in 6FDA-IPDA/-ceramic composite membranes as a function of the concentration of polymer in the casting solution. As is indicated, the flux decreases with an increase in polymer concentration.

TABLE 2

Gas Flux Results for 6FDA-IPDA Composite Membranes

| Polymer Conc. (wt %) | Gas Flux $N_2$ | Gas Flux $O_2$ ($10^{-6}$ cc(STP)/cm²s cmHg) | Gas Flux He | Gas Selectivities $O_2/N_2$ | Gas Selectivities $He/N_2$ | l** (μm) |
|---|---|---|---|---|---|---|
| 0.11 | 8.4 | 38.2 | 276.8 | 4.6 | 33.0 | 0.16 |
| 0.12 | 6.3 | 28.5 | 192.6 | 4.5 | 30.6 | 0.21 |
| 0.20 | 2.9 | 15.0 | 117.5 | 5.2 | 40.5 | 0.45 |
| 0.32 | 3.1 | 14.6 | 101.2 | 4.7 | 32.7 | 0.42 |
| 0.35 | 3.7 | 18.0 | 105.2 | 4.9 | 28.4 | 0.35 |
| 0.43 | 1.2 | 5.4 | 40.5 | 4.6 | 33.7 | 1.08 |
| 0.45 | 1.6 | 7.6 | 47.3 | 4.8 | 29.6 | 0.81 |
| 0.67 | 1.1 | 5.6 | 41.7 | 5.1 | 37.9 | 1.18 |
| 1.20 | 0.7 | 3.5 | — | 5.0 | — | 1.86 |
| Dense Film Permeability*/Selectivity | 1.3 | 6.7 | 59.2 | 5.1 | 45.5 | |

*Permeabilities in Barrers. 1 Barrer = 1 × $10^{-10}$ (cc(STP) cm)/(cm² cmHg sec)
**Film thickness calculated using dense film permeability for nitrogen.

TABLE 3

Gas Flux Results for Other Polymer Composite Membranes

| Polymer | Film Type (Composite or Dense)$^a$ | Gas Flux or Permeability$^b$ $N_2$ | $O_2$ | Helium (GPU or Barrer) | Gas Selectivities $O_2/N_2$ | $He/N_2$ | $He/O_2$ | l$^c$ (μm) |
|---|---|---|---|---|---|---|---|---|
| 6FDA-MDA | Composite | 2.9 | 14.4 | 125.3 | 5.0 | 43.2 | 8.7 | 0.28 |
| 6FDA-MDA | Dense | 0.8 | 4.6 | 50.0 | 5.7 | 61.7 | 10.9 | |
| TMHFPC | Composite | 12.9 | 52.2 | 262.9 | 4.0 | 20.4 | 5.0 | 0.60 |
| TMHFPC | Dense | 7.8 | 32.0 | 200.0 | 4.1 | 25.6 | 6.3 | |
| TMHFPSF | Composite | 4.8 | 22.3 | 142.7 | 4.7 | 29.7 | 6.4 | 0.91 |
| TMHFPSF | Dense | 4.0 | 18.0 | 113.0 | 4.5 | 28.3 | 6.3 | |

$^a$Film Type: "Composite" indicates composite membrane "Dense" indicates dense film
$^b$Gas Flux corresponds to composite membrane data, permeability corresponds to dense film data. Fluxes are reported in GPU (1 GPU = 1 × $10^{-6}$ cc/(cm₂*cmHg*sec)) Permeabilities are reported in Barrers (1 Barrer = 1 × $10^{-10}$ cc*cm/(cm²*cm(STP) Hg*sec))
$^c$Polymer Film layer thickness calculated using dense film nitrogen permeability.

It is believed that polymers having swollen coil diameters which are larger than the pores of the support can produce selective films. Those polymers having swollen coil diameters which are smaller than the pores of the support will not be sieved out of the solution and are able to pass into the pores of the ceramic. The amount of polymer applied to the surface of the support is carefully controlled to produce a polymer layer of less than about 0.5 μm. If an excessive amount of this polymer migrates into the pores of the support, there may not be enough polymer to produce a complete surface coating and/or the pores of the ceramic filter will become plugged with polymer.

The diameters of the swollen polymer coils in the casting solvent, methylene chloride, are tabulated in Table 4. These values were obtained from gel permeation chromatography measurements and from the following proposed by Flory:

$$[\eta]M = \Phi V_h \quad (2)$$

where $\Phi$ is a constant of value $2.8 \times 10^{21}$ and $V_h$ is the hydrodynamic volume of the polymer coil. For purposes of calculation, the polymer was assumed to be spherical.

TABLE 4

Molecular Volume of Polymers

| Polymer | Swollen Polymer Coil Diameter in Methylene Chloride (Å) |
|---|---|
| 6FDA-IPDA | 192 |
| 6FDA-MDA | 230 |
| TMHFPC | 330 |
| TMHFPSF | 280 |

Examination of the results in Table 4 indicates that all of the polymers tested possessed coil diameters of approximately 200 Å or larger. Thus, all were larger than the pores of the ceramic filter, and formed thin, defect-free membranes.

Effect of Temperature on Membrane Performance

The results presented thus far have represented the performance of polymer-ceramic composite membranes at ambient temperature. It is known that changes in temperature directly affect the physical properties of a polymer, increasing productivity and generally decreasing the separation ability of the membrane. Therefore, the gas transport properties of polyimide-ceramic composite membranes useful in this invention were measured as a function of temperature to temperatures of 570° F.

Figure 1:
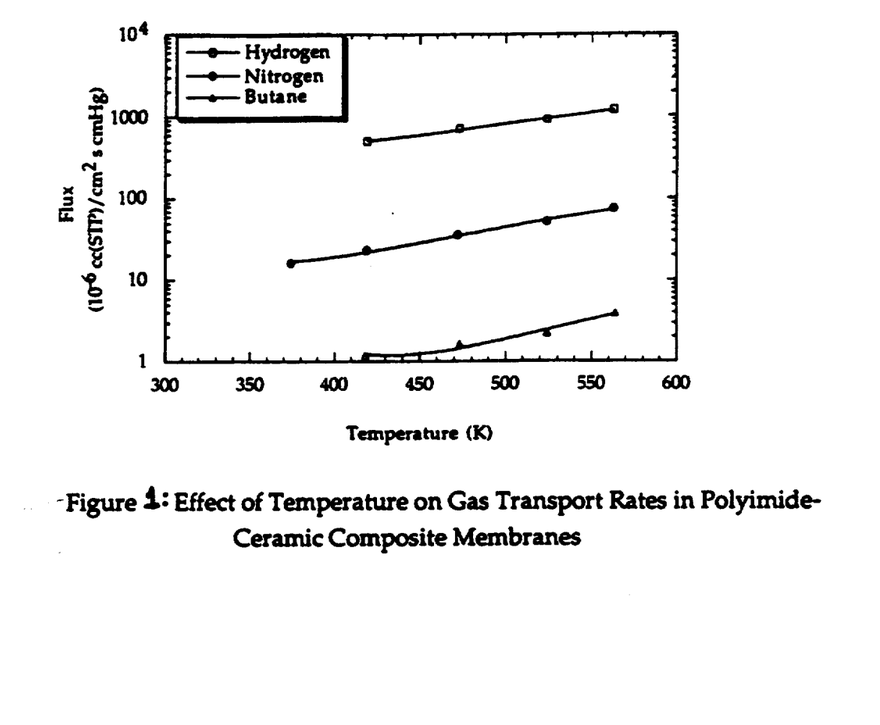
FIG. 1 is a graph of temperature versus gas flux properties of a polyimide-ceramic composite membrane.

The gas flux properties of a polyimide-ceramic composite membrane with a polymer layer thickness of approximately 1500 Å over the temperature range 212° F. to 572° F. are presented in FIG. 1 for hydrogen, nitrogen and butane. Nitrogen is provided as a reference penetrant. Low molecular weight hydrocarbons, such as methane, would be expected to behave in a manner similar to nitrogen. The results indicate that the productivity of the material increases dramatically with temperature. The productivity of the membrane for hydrogen at 570° F. is 17.6 ft³(STP)/ft² day psi.

Figure 2:
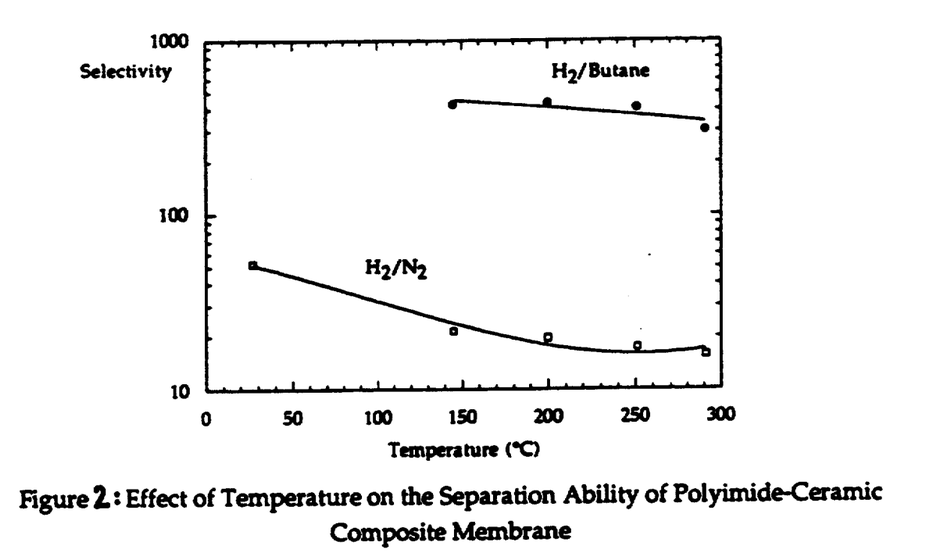
FIG. 2 is a graph of temperature versus selectivity of a polyimide-ceramic composite membrane.

The selectivity of the membrane for the separation of hydrogen from butane and hydrogen from nitrogen are presented in FIG. 2. The selectivities of the membrane at 570° F. (299° C.) for these gas pairs are about 300 and 16, respectively. The selectivities for both gas pairs decreases with temperature over the temperature range studied.

Evaluation of the properties of these membranes at 600° F. was also performed. Attempts to complete permeation experiments at this temperature were unsuccessful. As an alternative, the gas transport properties of a number of polyimide-ceramic composite membranes were measured. The membranes were heated in an oven blanketed with helium at 660° F. The membranes were held at this temperature for times ranging from 2 to 10 hours. Following the heating, the membranes were cooled and their properties measured at room temperature. The results for two representative samples are shown in Table 5.

TABLE 5

Effect of heating Polyimide-Ceramic Composite Membranes to 660° F.
All data reported here was measured at 80° F.,
$\Delta p = 50$ psig, pure gases

| Membrane | Prior to Heating | | After Heating | |
|---|---|---|---|---|
| | Nitrogen Flux (GPU) | $\alpha$ He/N$_2$ | Nitrogen Flux (GPU) | Selectivity He/N$_2$ |
| A (2 hr heat) | 2.7 | 48.3 | 19.3 | 10.2 |
| B (6.5 hr heat) | 24.8 | 9.2 | 247.5 | 3.1 |

1 GPU = $10^{-6}$ cc (STP)/cm$^2$ sec cmhg

It is clear that the separation ability of the membranes is dramatically reduced by this treatment. This result is consistent with the inability to obtain stable operation when it was attempted to measure gas permeation rates at 660° F. While not being bound by any theory, it is believed that as the polymer is heated to 660° F., the mechanical strength of this material is seriously impaired. Note that the glass transition temperature of this material is only about 590° F. Therefore, the polymer may be acting as a rubber at 660° F. As a rubber, the polymer apparently has the ability to begin to flow into the ceramic filter which acts as a support. As the polymer flows into the support, defects are created on the surface of the membrane. These defects, which can be thought of as holes, are not gas selective and provide no resistance to gas flow. Therefore, when defects are created, the selectivity of the membrane is reduced and the gas flux rates will increase. This behavior is clearly present in the membranes tested.

The formation of surface defects as a result of heating is an intrinsic property of the polymer used. Results indicate that 6FDA-IPDA polyimide is suitable for use at temperatures to 570° F., but degrades at 660° F. and is not stable there.

Dehydrogenation Catalysts

A variety of dehydrogenation catalysts may be used in the present invention. These include zeolitic materials as well as non-zeolitic materials, with the zeolites being preferred.

The present invention will now be described by reference to a particularly preferred dehydrogenation catalyst, though it is understood that other dehydrogenation catalysts may used in the process of this invention.

The preferred catalyst for use in this invention is a zeolite. The zeolite component of this preferred dehydrogenation catalyst is generally referred to herein as zeolite, but also is commonly referred to as a crystalline silicate or silicate.

The term "alkali" is used herein to mean Group IA metals. Preferred alkali metals for use in the catalyst of the present invention are sodium, potassium, cesium, lithium and rubidium. Sodium and potassium are more preferred. Sodium is the most preferred alkali metal for use in the catalyst.

The amount of alkali must be lower than the levels typically taught in the prior art for "non-acidic" catalysts. The amount of alkali will vary depending on the ratio of silica to alumina in the zeolite component of the catalyst, with less alkali being required as the silica to alumina ratio of the zeolite increases. Preferred alkali amounts, where the alkali is sodium, for example, for the catalyst where the silica to alumina ratio is 500:1 are about 750 ppm to about 3800 ppm.

Amounts of alkali are by weight based on the total weight of the zeolite component of the catalyst. The abbreviation ppm indicates parts per million.

The amount of alkali is an amount sufficient to neutralize substantially all of the acidity of the zeolite. Preferred amounts of alkali are between one and five parts alkali to one part aluminum, more preferably between one and three parts alkali to one part aluminum on a molar basis, based on the aluminum in the zeolite. Thus, the amount of alkali will vary as a function of aluminum. Typical preferred lower amounts of alkali are 0.01, more typically 0.1 wt %. In most cases, some alkali is present in the zeolite that cannot be readily ion exchanged out of the silicate on a practical basis. This difficult to exchange alkali can be minimized by selecting appropriate methods of preparing the silicate, for instance, as disclosed in Example 1 hereinbelow.

The zeolite of the catalyst of the present invention preferably is low in acidity, more preferably substantially free of acidity. However, the low acidity zeolite, or zeolite substantially free of acidity, is, in accordance with the present invention, not achieved by using large amounts of alkali. The low acidity, or substantial non-acidity, may be achieved by a combination of low aluminum content in the zeolite and the use of low amounts of alkali and/or the use of alkaline earth metals. The silicate component of the catalyst preferably is included in a matrix or binder to form the finished catalyst, as described hereinbelow. Preferably, the finished catalyst is of low acidity, more preferably substantially free of acidity.

The acidity of the zeolite may be determined as follows: 0.1–1.5 g of zeolite is mixed with 1 g of acid-washed and neutralized alundum and packed in a 3/16" stainless steel reactor tube with the remaining space filled with alundum. The reactor contents are calcined for one hour at 450° C. The reactor is then-placed in a clam-shell furnace at 427° C. and the reactor outlet connected to the inlet of a gas chromatograph. The inlet is connected to the carrier gas line of the GC. Helium is passed through the system at 30 cc/min. 0.04 Microliter pulses of n-decane are injected through a septum above the reactor and reaction products are determined by standard GC analysis. Blank runs with alundum should show no conversion under the experimental conditions, nor should a 100% Catapal alumina catalyst.

A pseudo-first-order, cracking rate constant, k, is calculated using the formula:

$$k = \frac{1}{A} \ln \frac{1}{1-x}$$

where A is the weight of silicate in grams and x is the fractional conversion to products boiling below decane. The silicate is substantially free of acidity when the value of 1 n k is less than about −3.8. The silicate is low in acidity if Ink is less than about −2.3.

The zeolite as described below, may be a component of the final catalyst, for instance where the final catalyst is a zeolite "bound" in a matrix such as silica or alumina. In such case, the zeolite acidity should be determined by measuring acidity of the zeolite as a separate component.

The acidity of the finished catalyst containing the zeolite may also be assessed as described above.

In accordance with an alternate preferred embodiment of the catalysts used in the present invention, an alkaline earth metal (Group IIA metal) is also included in the catalyst. Magnesium, calcium, strontium and barium are, preferred Group IIA metals. Magnesium is a more preferred Group IIA metal for use in the catalyst of the present invention. The alkaline earths are advantageously used to reduce the acidity of the catalyst. The alkaline earth metals are not as effective as the alkali metals in reducing acidity, but it has been found that the alkaline earth metals do not impart as much sulfur sensitivity to the catalyst as do the alkali metals. In this preferred alternate embodiment, alkaline earth metals are included in the zeolite in an amount between 0.1 to 10.0, preferably 0.5 to 5.0, parts of alkaline earth metal per part alkali metal, on a molar basis.

Additionally, the acid sites can advantageously be neutralized with other basic components such as cerium or lanthanum.

An important aspect of the present invention is the sulfur tolerance of the preferred catalyst. Sulfur tolerance is used herein primarily to connote that the catalyst may be exposed to substantial amounts of sulfur, such as more than 2 ppm sulfur, and return to relatively high activity after the exposure to high sulfur levels is discontinued. It has also been found that the preferred catalyst of the present invention has a surprising resistance to sulfur poisoning or deactivation in the range of about 0.1 to 2 ppm sulfur. Thus, in addition to the catalyst capability of "bouncing back" in activity after discontinuance of sulfur in the feed, the catalyst also can "resist" or tolerate, as a steady component in the feed, up to 2 ppm sulfur, more preferably up to 1 ppm sulfur, most preferably up to 0.5 ppm sulfur. Accordingly, the terminology "sulfur tolerance" is used herein to embrace the preferred catalyst's capability to regain activity after discontinuance of exposure to dehydrogenation sulfur and also the catalyst's ability to perform well (low fouling rate and good activity) in the presence of moderate amounts of sulfur.

The sulfur tolerance can be utilized in various ways. The feed to the process may contain relatively high amounts of sulfur compared to feed to other catalytic dehydrogenation processes using zeolitic-based catalysts, or the feed may be subject to periodic exposure to high amounts of sulfur (and hence the dehydrogenation zone subject to periodic high amounts of sulfur).

By "periodic exposure" is meant sulfur increases in the feed and hence in the dehydrogenation zone, for example, due to upsets in desulfurization steps upstream of the catalytic dehydrogenation zone, or breakthroughs or notable rises in the amount of sulfur in the feed due to the upstream sulfur removal steps, or simply due to changes in the base feedstock to the refinery or catalytic dehydrogenation zone. "Periodic" exposure is used to connote exposure to the specified sulfur levels for a significant period of time as opposed to continuous exposure to sulfur. A significant period of time would typically be at least 2 minutes, more typically an hour or more.

When dehydrogenation is carried out using a highly sulfur sensitive zeolite catalyst, it is necessary to go to substantial expense to reduce the sulfur in the feed to very low levels. Frequently, extensive guard bed and/or sulfur sorbent systems are used. Even in a situation where the sulfur content of the feed to the dehydrogenation zone will normally be very low, the preferred catalyst of the present invention is advantageously used as the preferred catalyst will tolerate exposure to sulfur; that is, the preferred catalyst shows much better activity restoration upon discontinuing the exposure to high sulfur levels. Thus, when using the preferred catalyst of the present invention, the capital cost of a dehydrogenation unit can be reduced, as less sulfur guard or sulfur removal equipment is needed to protect the catalytic dehydrogenation zone as is the case with other zeolite catalysts.

Although the process of the present invention is found to be a sulfur tolerant process, nonetheless, it is preferred not to subject the catalyst in the dehydrogenation zone to gross amounts of sulfur. Thus, preferably the sulfur in the feed is not above about dehydrogenation ppm, more preferably not above 10 ppm, and most preferably not above about 2 ppm. Especially preferred sulfur levels are between 0.1 and 1 ppm.

Amounts of sulfur are by weight based on the feed hydrocarbon to the process. Also, the sulfur is calculated on the basis of elemental sulfur, although the sulfur may be in the form of organic sulfur compounds or in the form of hydrogen sulfide.

Preferred feeds for the dehydrogenation process of the present invention include light alkane or paraffin rich streams containing $C_2$–$C_5$, and preferably $C_3$ and $C_4$ alkanes. For example, a preferred feed is a paraffin rich raffinate obtained from solvent extraction or molecular sieve extraction of paraffins from a mixture of paraffins and aromatics. Another preferred feed is a light distillate stream from a fluid catalytic cracker which is rich in $C_5^-$ paraffins.

The preferred catalyst of the present invention uses a ZSM-5 Type intermediate pore size zeolite material. ZSM-5 and ZSM-11 are examples of a ZSM-5 type zeolite. One preferred material is silicalite or very high ratio silica to alumina form of ZSM-5.

Table 6 below reports the X-ray diffraction pattern for ZSM-5 as given in the Argauer patent (U.S. Pat. No. 3,702,886).

TABLE 6

| Interplanar Spacing d (A) | Relative Intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 } ± 0.1<br>5.97 } | w. |
| 5.56 ± 0.1 | w. |
| 5.01 ± 0.1 | w. |
| 4.60 ± 0.08 | w. |
| 4.25 ± 0.08 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

Also as reported in the Argauer patent, the values in Table 6 were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/$I_o$, where $I_o$ is the intensity of the strongest line or peak, and d (obs.), the interplanar spacing in A, corresponding to the recorded lines, were calculated. In Table 6, the relative intensities are given in terms of the symbols s.=strong, m.=medium, m.s.=medium strong, m.w.=medium weak and v.s.=very. strong. It should be understood that this X-ray diffraction pattern is characteristic of all the species of ZSM-5 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it had been subjected to thermal treatment.

ZSM-5 is regarded by many to embrace "silicalite" as disclosed in U.S. Pat. No. 4,061,724 to Grose et al. For ease of reference herein, silicalite is referred to as a ZSM-5-type material with a very high silica to alumina ratio and is regarded as embraced within the ZSM-5 X-ray diffraction pattern. The silica to alumina ratio is on a molar basis of silica ($SiO_2$) to alumina ($Al_2O_3$).

Various references disclosing silicalite and ZSM-5 are provided in U.S. Pat. No. 4,401,555 to Miller. These references include the aforesaid U.S. Pat. No. 4,061,724 to Grose et al.; U.S. Pat. No. Re. 29,948 to Dwyer et al.; Flanigen et al., Nature, 271, 512–516 (Feb. 9, 1978) which discusses the physical and adsorption characteristics of silicalite; and Anderson et al., *J. Catalysis* 58, 114–130 (1979) which discloses catalytic reactions and sorption measurements carried out on ZSM-5 and silicalite. The disclosures of these references and U.S. Pat. No. 4,401,555 are incorporated herein by reference, particularly including their disclosures on methods of making high silica to alumina zeolites having an X-ray diffraction pattern in substantial accord with Table 6.

Other zeolites which can be used in the preferred catalyst of the present invention include those as listed in U.S. Pat. No. 4,835,336; namely: ZSM-11, ZSM-12, ZSM-22, ZSM-23, ZSM-35, ZSM-38, ZSM-48, and other similar materials.

ZSM-5 is more particularly described in U.S. Pat. No. 3,702,886 and U.S. Pat. Re. 29,948, the entire contents of which are incorporated herein by reference.

ZSM-11 is more particularly described in U.S. Pat. No. 3,709,979 the entire contents of which are incorporated herein by reference. Bibby et al., Nature, 280, 664–665 (Aug. 23, 1979) reports the preparation of a crystalline silicate called "silicalite-2".

ZSM-12 is more particularly described in U.S. Pat. No. 3,832,449, the entire contents of which are incorporated herein by reference.

ZSM-22 is more particularly described in U.S. Pat. Nos. 4,481,177, 4,556,477 and European Patent No. 102,716, the entire contents of each being expressly incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

ZSM-48 is more particularly described in U.S. Pat. No. 4,397,827 the entire contents of which are incorporated herein by reference.

Of these, ZSM-5, ZSM-11, ZSM-22 and ZSM-23 are preferred. ZSM-5 is most preferred for use in the catalyst of the present invention.

Additionally, zeolites SSZ-20, SSZ-23 and SSZ-32 may be used. SSZ-20 is disclosed in U.S. Pat. No. 4,483,835, SSZ-23 is disclosed in U.S. Pat. No. 4,859,442, and SSZ-32 is disclosed in U.S. Pat. No. 5,053,373, each of which is incorporated herein by reference.

The crystalline silicate may be in the form of a borosilicate, where boron replaces at least a portion of the aluminum of the more typical aluminosilicate form of the silicate. Borosilicates are described in U.S. Pat. Nos. 4,268,420; 4,269,813; and 4,327,236 to Klotz, the disclosures of which patents are incorporated herein, particularly that disclosure related to borosilicate preparation.

In the borosilicate used in the process and catalyst of the present invention, the preferred crystalline structure is that of ZSM-5, in terms of X-ray diffraction pattern. Boron in the ZSM-5 type borosilicates takes the place of aluminum that is present in the more typical ZSM-5 crystalline aluminosilicate structures. Borosilicates contain boron in place of aluminum, but generally there is some trace amounts of aluminum present in crystalline borosilicates.

Still further crystalline silicates which can be used in the preferred catalyst of the present invention are ferrosilicates, as disclosed for example in U.S. Pat. No. 4,238,318, gallosilicates, as disclosed for example in U.S. Pat. No. 4,636,483, and chromosilicates, as disclosed for example in U.S. Pat. No. 4,299,808.

Thus, various high silica content silicates (silicates having a high ratio of silica to other constituents) can be used as the zeolite component of the preferred catalyst of the present invention.

Borosilicates and aluminosilicates are preferred silicates for use in the present invention. Aluminosilicates are the most preferred. Silicalite is a particularly preferred aluminosilicate for use in the preferred catalyst of the present invention.

As synthesized, silicalite (according to U.S. Pat. No. 4,061,724) has a specific gravity at 77° F. of 1.99±0.05 g/cc as measured by water displacement. In the calcined form (1112° F. in air for one hour), silicalite has a specific gravity of 1.70±0.05 g/cc. With respect to the mean refractive index of silicalite crystals, values obtained by measurement of the as synthesized form and the calcined form (1112° F. in air for one hour) are 1.48±0.01 and 1.39±0.01, respectively.

The X-ray powder diffraction pattern of silicalite (1112° F. calcination in air for one hour) has six relatively strong lines (i.e., interplanar spacings). They are set forth in Table 7 ("S"-strong, and "VS"-very strong):

TABLE 7

| d-A | Relative Intensity |
|---|---|
| 11.1 ± 0.2 | VS |
| 10.0 ± 0.2 | VS |

TABLE 7-continued

| d-A | Relative Intensity |
|---|---|
| 3.85 ± 0.07 | VS |
| 3.82 ± 0.07 | S |
| 3.76 ± 0.05 | S |
| 3.72 ± 0.05 | S |

Table 8 shows the X-ray powder diffraction pattern of a typical silicalite composition containing 51.9 moles of $SiO_2$ per mole of tetrapropyl ammonium oxide [$(TPA)_2O$], prepared according to the method of U.S. Pat. No. 4,061,724, and calcined in air at 1112° F. for one hour.

TABLE 8

| d-A | Relative Intensity |
|---|---|
| 11.1 | 100 |
| 10.02 | 64 |
| 9.73 | 16 |
| 8.99 | 1 |
| 8.04 | 0.5 |
| 7.42 | 1 |
| 7.06 | 0.5 |
| 6.68 | 5 |
| 6.35 | 9 |
| 5.98 | 14 |
| 5.70 | 7 |
| 5.57 | 8 |
| 5.36 | 2 |
| 5.11 | 2 |
| 5.01 | 4 |
| 4.98 | 5 |
| 4.86 | 0.5 |
| 4.60 | 3 |
| 4.44 | 0.5 |
| 4.35 | 5 |
| 4.25 | 7 |
| 4.08 | 3 |
| 4.00 | 3 |
| 3.85 | 59 |
| 3.82 | 32 |
| 3.74 | 24 |
| 3.71 | 27 |
| 3.64 | 12 |
| 3.59 | 0.5 |
| 3.48 | 3 |
| 3.44 | 5 |
| 3.34 | 11 |
| 3.30 | 7 |
| 3.25 | 3 |
| 3.17 | 0.5 |
| 3.13 | 0.5 |
| 3.05 | 5 |
| 2.98 | 10 |

Silicalite crystals in both the "as synthesized" and calcined forms are generally orthorhombic and have the following unit cell parameters: a=20.05 A, b=19.86 A, c=13.36 A (all values ±0.1 A).

The pore diameter of silicalite is about 6 Å and its pore volume is 0.18 cc/gram as determined by adsorption. Silicalite adsorbs neopentane (6.2 A kinetic diameter) slowly at ambient room temperature. The uniform pore structure imparts size-selective molecular sieve properties to the composition, and the pore size permits separation of p-xylene from o-xylene, m-xylene and ethyl-benzene as well as separations of compounds having quaternary carbon atoms from those having carbon-to-carbon linkages of lower value (e.g., normal and slightly branched paraffins).

The crystalline silicates of U.S. Pat. No. Re. 29,948 (Reissue of U.S. Pat. No. 3,702,886 to Argauer) are disclosed as having a composition, in the anhydrous state, as follows:

$$0.9 \pm 0.2 \, [xR_2O + (1 - x)M_{2/n}O]: <.005$$
$$Al_2O_3: > 1 \, SiO_2$$

where M is a metal, other than a metal of Group IIIA, n is the valence of said metal, R is an alkyl ammonium radical, and x is a number greater than 0 but not exceeding 1. The crystalline silicate is characterized by the X-ray diffraction pattern of Table 6, above.

The crystalline silicate polymorph of U.S. Pat. No. 4,073,865 to Flanigen et al. is related to silicalite and, for purposes of the present invention, is regarded as being in the ZSM-5 class. The crystalline silicate exhibits the X-ray diffraction pattern of Table 9.

TABLE 9

| d (A) | Intensity |
|---|---|
| 11.14 | 91 |
| 10.01 | 100 |
| 9.75 | 17 |
| 8.99 | 1 |
| 8.01 | 0.5 |
| 7.44 | 0.5 |
| 7.08 | 0.2 |
| 6.69 | 4 |
| 6.36 | 6 |
| 5.99 | 10 |
| 5.71 | 5 |
| 5.57 | 5 |
| 5.37 | 1 |
| 5.33 | 1 |
| 5.21 | 0.3 |
| 5.12 | 1.5 |
| 5.02 | 3 |
| 4.97 | 6 |
| 4.92 | 0.6 |
| 4.72 | 0.5 |
| 4.62 | 2 |
| 4.47 | 0.6 |
| 4.36 | 3 |
| 4.25 | 4 |
| 4.13 | 0.5 |
| 4.08 | 1.5 |
| 4.00 | 3 |
| 3.85 | 44 |
| 3.82 | 25 |
| 3.71 | 21 |
| 3.65 | 5 |
| 3.62 | 5 |
| 3.59 | 1 |
| 3.48 | 1.5 |
| 3.45 | 3 |
| 3.44 | 3 |
| 3.35 | 3 |
| 3.31 | 5 |
| 3.25 | 1.5 |
| 3.23 | 0.8 |
| 3.22 | 0.5 |

For purposes of the present invention, silicalite is regarded as being in the ZSM-5 class, being a form of ZSM-5 having a very high silica to alumina ratio; silicalite-2 is regarded as being in the ZSM-11 class.

The preparation of zeolites useful in the present invention generally involves the hydrothermal crystallization of a reaction mixture comprising water, a source of silica, and an organic templating compound at a Ph of 10 to 14. Representative templating moieties include quaternary cations such as $XR_4$ where X is phosphorous or nitrogen and R is an alkyl radical containing from 2 to 6 carbon atoms, e.g., tetrapropylammonium hydroxide (TPA-OH) or halide, as well as alkyl hydroxyalkyl compounds, organic amines and diamines, and heterocycles such as pyrrolidine.

When the organic templating compound (i.e., TPA-OH) is provided to the system in the hydroxide form in sufficient quantity to establish a basicity equivalent to the Ph of 10 to 14, the reaction mixture may contain only water and a reactive form of silica as additional ingredients. In those cases in which the Ph must be increased to above 10, ammonium hydroxide or alkali metal hydroxides can be suitably employed for that purpose, particularly the hydroxides of lithium, sodium and potassium. The ratio: $R^+$ to the quantity $R^+$ plus $M^+$, where $R^+$ is the concentration of organic templating cation and $M^+$ is the concentration of alkali metal cation, is preferably between 0.7 and 0.98, more preferably between 0.8 and 0.98, most preferably between 0.85 and 0.98.

The source of silica in the reaction mixture can be wholly, or in part, alkali metal silicate. Other silica sources include solid reactive amorphous silica, e.g., fumed silica, precipitated silica, silica sols, silica gel, and organic orthosilicates. One commercial silica source is Ludox AS-30, available from Du Pont.

Aluminum, usually in the form of alumina, is easily incorporated as an impurity into the zeolite. Aluminum in the zeolite contributes acidity to the catalyst, which is undesirable. To minimize the amount of aluminum, care should be exercised in selecting a silica source with a minimum aluminum content. Commercially available silica sols can typically contain between 500 and 700 ppm alumina, whereas fume silicas can contain between 80 and 2000 ppm of alumina impurity. As explained above, the silica to alumina molar ratio in the zeolite of the preferred catalyst used in the present invention is preferably greater than 30:1, more preferably greater than 200:1, most preferably greater than 500:1.

The quantity of silica in the reaction system is preferably between about 1 and 10 moles $SiO_2$ per mole-ion of the organic templating compound. Water should be generally present in an amount between 10 and 700 mole per mole-ion of the quaternary cation. The reaction preferably occurs in an aluminum-free reaction vessel which is resistant to alkali or base attack, e.g., Teflon.

In forming the final catalyst used in the present invention, the zeolite is preferably bound with a matrix. The term "matrix" includes inorganic compositions with which the silicate can be combined, dispersed, or otherwise intimately admixed. Preferably, the matrix is not catalytically active in a hydrocarbon cracking sense, i.e., contains substantially no acid sites. Satisfactory matrices include inorganic oxides. Preferred inorganic oxides include alumina, silica, naturally occurring and conventionally processed clays, for example bentonite, kaolin, sepiolite, attapulgite and halloysite. Preferred matrices are substantially non-acidic and have little or no cracking activity. Silica matrices and also alumina matrices are especially preferred. It has been found that the use of a low acidity matrix, more preferably a substantially non-acidic matrix, is advantageous in the catalyst of the present invention.

Compositing the zeolite with an inorganic oxide matrix can be achieved by any suitable method wherein the zeolite is intimately admixed with the oxide while the latter is in a hydrous state (for example, as a hydrous salt, hydrogel, wet gelatinous precipitate, or in a dried state, or combinations thereof). A convenient method is to prepare a hydrous mono or plural oxide gel or cogel using an aqueous solution of a salt or mixture of salts (for example, aluminum sulfate and sodium silicate). Ammonium hydroxide carbonate (or a similar base) is added to the solution in an amount sufficient to precipitate the oxides in hydrous form. Then, the precipitate is washed to remove most of any water soluble salts and it is thoroughly admixed with the zeolite which is in a finely divided state. Water or a lubricating agent can be added in an amount sufficient to facilitate shaping of the mix (as by extrusion).

A preferred zeolite for use in the catalyst of the present invention is ZSM-5 having a very high silica to alumina ratio, which, for convenience, is frequently referred to herein as "silicalite". Assuming that the only crystalline phase in the silicalite prep is silicalite, the silicalite preferably has a percent crystallinity of at least 80%, more preferably at least 90%, most preferably at least 9.5%. To determine percent crystallinity, an X-ray diffraction (XRD) pattern of the silicalite is made and the area under the eight major peaks is measured in the angle interval between 20.5 and 25.0 degrees. Once the area under the curve is calculated, it is compared with the area under the curve for a 100% crystalline standard for silicalite.

The preferred crystallite size of the zeolite is less than 10 microns, more preferably less than 5 microns, still more preferably less than 2 microns, and most preferably less than 1 micron. When a crystallite size is specified, preferably at least 70 wt % of the crystallites are that size, more preferably at least 80 wt %, most preferably 90 wt %. Crystallite size can be controlled by adjusting synthesis conditions, as known to the art. These conditions include temperature, Ph, and the mole ratios $H_2O/SiO_2$, $R^+/SiO_2$, and $M^+/SiO_2$, where $R^+$ is the organic templating cation and $M^+$ an alkali metal cation. For small crystallite size, i.e., less than 10 microns, typical synthesis conditions are listed below:

|  | Preferred | More Preferred | Most Preferred |
| --- | --- | --- | --- |
| Temperature, °F. | 176–392 | 194–356 | 212–302 |
| pH | 12–14 | 12.5–14 | 13–13.5 |
| $H_2O/SiO_2$ | 3–100 | 3–50 | 3–40 |
| $R^+/SiO_2$ | 0.1–1.0 | 0.1–0.5 | 0.2–0.5 |
| $M^+/SiO_2$ | 0.01–0.3 | 0.01–0.15 | 0.01–0.08 |

Other techniques known to the art, such as seeding with zeolite crystals, can be used to reduce crystallite size.

The zeolite component of the catalyst of the present invention has an intermediate pore size. By "intermediate pore size" as used herein is meant an effective pore aperture in the range of about 5 to 6.5 Angstroms when the zeolite is in the H-form. Zeolites having pore apertures in this range tend to have unique molecular sieving characteristics. Unlike small pore crystalline silicates or zeolites such as erionite, they will allow hydrocarbons having some branching into the zeolitic void spaces. Unlike large pore zeolites such as the faujasites, they can differentiate between n-alkanes and slightly branched alkanes on the one hand and larger branched alkanes having, for example, quaternary carbon atoms.

The effective pore size of the crystalline silicates or zeolites can be measured using standard adsorption techniques and hydrocarbonaceous compounds of known minimum kinetic diameters. See Breck, *Zeolite Molecular Sieves*, 1974 (especially Chapter 8) and Anderson et al., *J. Catalysis* 58, 114 (1979), both of which are incorporated by reference.

Intermediate pore size crystalline silicates or zeolites in the H-form will typically admit molecules having kinetic diameters of 5 to 6. Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular zeolite, but do not penetrate as quickly and in some cases, are effectively excluded (for example, 2,2-dimethylbutane is excluded from H-ZSM-5). Compounds having kinetic diameters in the range of 6 to 6.5 Angstroms include: cyclohexane (6.0), m-xylene (6.1) and 1,2,3,4-tetramethylbenzene (6.4). Generally, compounds having kinetic diameters of greater than about 6.5 Angstroms cannot penetrate the pore apertures and thus cannot be adsorbed in the interior of the zeolite. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. ZSM-5, ZSM-11 and silicalite, for example, fall within this range.

In performing adsorption measurements to determine pore size, standard techniques are used. It is convenient to consider a particular molecule as excluded if it does not reach at least 95% of its equilibrium adsorption value on the zeolite in less than about 10 minutes (P/Po=0.5 25° C.).

Examples of intermediate pore size zeolite include silicalite and members of the ZSM series such as ZSM-5, ZSM-11, ZSM-12, ZSM-21, ZSM-22, ZSM-23, ZSM-35, ZSM-38, SSZ-20, SSZ-23 SSZ-32.

The catalysts according to the present invention contain one or more noble metals. Preferred metals are rhodium, palladium, iridium or platinum. Palladium, and platinum are more preferred. Platinum is most preferred. The preferred percentage of the noble metal, such as platinum, in the catalyst is between 0.1 wt % and 5 wt %, more preferably from 0.3 wt % to 2.5 wt %.

Noble metals are preferably introduced into the zeolite by impregnation, occlusion, or exchange in an aqueous solution or exchange in an aqueous solution of an appropriate salt. When it is desired to introduce two Group VIII metals into the zeolite, the operation may be carried out simultaneously or sequentially. Preferably, the Group VIII metal is finely dispersed within, and on, the zeolite. By way of example, platinum can be introduced by impregnation with an aqueous solution of tetraammineplatinum (II) nitrate, tetraammineplatinum (II) hydroxide, dinitrodiamino-platinum or tetraammineplatinum (II) chloride. In an ion exchange process, platinum can be introduced by using cationic platinum complexes such as tetraammineplatinum (II) nitrate or chloride. When platinum is introduced into the zeolite by occlusion, a platinum complex is preferably introduced into the zeolite during its formation.

After platinum impregnation, the catalyst is preferably ammonium exchanged, if necessary, to remove alkali metals. After the desired metal or metals have been introduced, the catalyst is preferably treated in air, or air diluted with an inert gas, and reduced in hydrogen. Catalysts containing platinum can be subjected to halogen or halide treatments to achieve or maintain a uniform metal dispersion. Typically, the halide is a chloride compound. The catalysts of this invention can be subjected to similar treatments although the preferred catalyst does not contain chloride in the final form.

The catalyst can be employed in any of the conventional types of catalytic dehydrogenation equipment. The catalyst can be employed in the form of pills, pellets, granules, broken fragments, or various special shapes within a reaction zone.

The light paraffinic hydrocarbon feed to the dehydrogenation zone is preferably a light hydrocarbon or naphtha fraction, preferably boiling below about 450° F., more preferably below about 250° F., and most preferably below about 150° F. This can include, for example, straight run naphthas, paraffinic raffinates from aromatic extraction, essentially pure $C_3$, $C_4$, $C_5$ streams or mixtures thereof, and $C_2$-$C_{10}$ paraffin-rich feeds, as well as paraffin-containing naphtha products from other refinery processes, such as hydrocracking or conventional reforming. The feed will preferably contain at least one of propane, butane, isobutane, or a mixture thereof. Preferably, paraffin-rich feeds contain greater than 0.5 wt % $C_2$-$C_{10}$ paraffins, and more preferably grater than 0.5 wt % $C_2$-$C_5$ paraffins. The actual dehydrogenation conditions will depend in large measure on the feed used, whether highly aromatic, paraffinic or naphthenic.

The feed may also contain unreactive gases (e.g., $N_2$ or methane) which can serve to reduce the reactant hydrocarbon partial pressures, thereby resulting in a more favorable thermodynamic equilibrium and greater conversion.

We have found that the catalyst of the present invention has greater stability (for yield) if the amount of water weight, more preferably less than 25 ppm.

In the process of the present invention, the pressure in the dehydrogenation reaction zone is preferably between subatmospheric and 100 psig, more preferably between subatmospheric and 25 psig, and most preferably between subatmospheric and 10 psig. The liquid hourly space velocity (LHSV—calculated on the basis of the volume amount, as a liquid at standard conditions, of hydrocarbon charged to the dehydrogenation zone per hour divided by the volume of the catalyst bed utilized) is preferably between about 0.1 to about 20 hr.$^{-1}$ with a value in the range of about 0.3 to about 5 hr.$^{-1}$ being preferred. The temperature is preferably between about 700° F. and about 1300° F., more preferably between about 800° F. and about 1100° F. and most preferably between about 800° F. and 1000° F. As is well known to those skilled in the dehydrogenation art, the initial selection of the temperature within this broad range is made primarily as a function of the desired conversion level of the paraffinic hydrocarbon considering the characteristics of the feed and of the catalyst. Thereafter, to provide a relatively constant value for conversion, the temperature is slowly increased during the run to compensate for the inevitable deactivation that occurs.

In accordance with one embodiment of the present invention, the dehydrogenation process is carried out in the absence added hydrogen. This favors increased yield of product olefins, and allows the dehydrogenation process to be operated at a lower temperature.

It has been found that the preferred catalysts of the present invention achieve particularly good selectivity to olefin production if they are presulfided prior to use in dehydrogenation. The sulfiding of the catalyst can be carried out in situ (in the dehydrogenation reactor or reactors) or ex situ. Preferably, the sulfiding is carried out in situ. Sulfiding techniques known in the art are suitable.

In the process embodiment of the present invention, the hydrocarbon feed is contacted with the catalyst as described above in a dehydrogenation zone or dehydrogenation reactor under dehydrogenation conditions. This contacting can be accomplished by using the catalyst in a fixed-bed system, a moving bed system, a fluidized system or in a batch-type operation; however, it is preferred to use either a fixed-bed system or a dense phase moving bed system.

In a fixed-bed system, typically the hydrocarbon feed is preheated to the desired reaction temperature and then passes into a dehydrogenation zone containing a fixed-bed of the catalyst. The process of the present invention can comprise the use of the catalyst as described above in one or more of the reactors in a series of dehydrogenation reactors or in a dehydrogenation zone which is simply a part of the overall train of reactors used in a dehydrogenation unit.

When the present process is conducted in a series of dehydrogenation reactors, each reactor after the first is preferably maintained at a higher average temperature than the temperature of the preceding reactor. It is more preferred to maintain each reactor after the first at least 10° F., and most preferred at least 20° F. in temperature higher than the preceding reactor in the series.

When two dehydrogenation reactors are employed in series, the polymer-ceramic composite membrane of this invention is located so that the effluent from the first reactor contacts the membrane before that effluent is passed to the second reactor. If more than two dehydrogenation reactors are used in series, the effluent from each reactor should contact the membrane before the effluent is passed to the next reactor in the series. In this way, hydrogen is separated from the effluent before it is passed to the next reactor.

It has been found that the catalyst of the present process may be rejuvenated to at least partially recover activity lost during use in the dehydrogenation process. Rejuvenation is typically conducted by flowing hydrogen over the catalyst in the substantial absence of a hydrocarbon feed at a temperature between about 1000° F. and about 1200° F. for between about 4 hours and about 48 hours, and preferably for between about 8 hours and about 24 hours. It has also been found that the catalyst is most effectively rejuvenated when the rate of catalyst deactivation during dehydrogenation is maintained at low levels, for example by restricting the reaction temperature of the dehydrogenation process to a maximum of at most about 1000° F. By a "substantial absence of hydrocarbon feed" is meant that hydrocarbon is not introduced to the catalyst during rejuvenation. Typically, liquid hydrocarbons are drained from the dehydrogenation reactor before rejuvenation, but it is not required that residual liquid remaining on the catalyst after the liquid is drained be flushed from the catalyst before rejuvenation.

EXAMPLE 1

Catalyst Preparation 80 grams of $NaNO_3$ were dissolved in 80 grams of distilled $H_2O$. 8.3 grams of $H_3BO_3$ were added with mixing, followed by 800 grams of a 25% aqueous solution of TPAOH and mixed for 10 minutes. 200 additional grams of 25% TPAOH and 800 grams of $H_2O$ were then added with mixing. Then 200 grams of a fumed silica (Cab-O-Sil M-5) were added and mixed for 10 minutes. The mixture was placed in a sealed Teflon bottle and heated at 100° C. for 7 days. The product was centrifuged, the supernatant removed, and the solids washed with distilled water. The solids were dried overnight in a vacuum oven at 110° C., then calcined in dry air for 8 hours at 538° C. The solids were identified as 100% silicalite by X-ray diffraction analysis. The average particle diameter, as determined by SEM, was about 0.5 microns. The catalyst was impregnated with 0.8% Pt using an aqueous solution of $Pt(NH_3)_4(NO_3)_2$ and the pore-fill method. The catalyst was dried overnight in a vacuum oven at 110° C., then calcined in dry air at 177° C. for 4 hours, 232° C. for 4 hours, and 288° C. for 4 hours. It was then exchanged twice at 80° C. using a 25% aqueous solution of ammonium acetate, filtered, then dried in a vacuum oven overnight at 110° C. The catalyst was then impregnated with 0.05% Na using an aqueous solution of $Na_2CO_3$ and the pore-fill method, then dried overnight in a vacuum oven at 110° C. and calcined in dry air for 4 hours at 260° C. The catalyst contained 264 ppm Al by ICP analysis, and had an alkali/Al molar ratio of about 2.

EXAMPLE 2

Catalyst Preparation

A silicalite sample containing 900 ppm Al was prepared. The sieve was impregnated with 0.3% Na using an aqueous solution of $NaNO_3$ and the pore-fill method. The sieve was dried overnight in a vacuum oven at 110° C. then calcined at 260° C. for 4 hours in dry air. It was then impregnated with 0.8% Pt using an aqueous solution of $Pt(NH_3)_4(N_3)_2$ and the pore-fill method, dried overnight in a vacuum oven at 110° C., then calcined in dry air at 149° C. for 2 hours, 204° C. for 2 hours, and 288° C. for 4 hours. The catalyst was then impregnated with 0.15% Mg using an aqueous solution of $Mg(N_3)_2$ and the pore-fill method, then dried and calcined by the same procedure used after Pt impregnation. The alkali-/Al molar ratio for this catalyst was about 4.

EXAMPLE 3

Catalyst Preparation

To 100 grams of silica (Hi-Sil 233, a hydrated silica manufactured by PPG) were added 8 grams of kaolin clay powder (53.7 wt % $SiO_2$, 42.5 wt % $Al_2O_3$) and 60 grams of a 40 wt % aqueous solution of TPAOH and mixed for 1 hour in a Baker-Perkins mixer. Then 0.34 grams of $H_3BO_3$ were dissolved in dehydrogenation grams of water and added to the above mixture along with 5.8 grams of a 50 wt % aqueous solution of NaOH. Mixing continued for another dehydrogenation minutes. The mixture was then extruded through a 1/16-inch die. The extrudate was placed in a sealed Teflon bottle and heated at 100° C. for 4 days. The extrudate was then dried overnight at 110° C. in a vacuum oven and calcined in air at 538° C. for 8 hours. The product was identified as about 100% ZSM-5 by X-ray diffraction analysis, and was composed of particles about 0.2 microns in diameter as determined by SEM. ICP analysis showed the catalyst to contain 1.5% Na and 1.4% Al, such that the alkali/Al molar ratio was about 1.3. The catalyst was impregnated with 0.8% Pt using an aqueous solution of $Pt(N_3)_4(NO_3)_2$ and the pore-fill method. The catalyst was then dried overnight in a vacuum oven at 110° C. and calcined in dry air for 4 hours at 204° C., 4 hours at 260° C., and 4 hours at 288° C.

Effect of Hydrogen Removal via Polymer-Ceramic Composite Membranes on Butane Dehydrogenation The ability of polyimide-ceramic composite membranes to affect the degree of conversion in a butane dehydrogenation reactor was measured. First, the properties of the dehydrogenation catalyst prepared in Example 3 were measured in a standard reactor.

Comparative Example A

Dehydrogenation Without Membrane

The reactors and associated tubing were surface treated to minimize the metal's catalytic activity. Following this treatment, catalyst was packed into the tubes using glass wool to hold the catalyst in the desired bed location. System start-up was as follows:

The system was leak checked with hydrogen at room temperature and any leaks eliminated prior to proceeding.

With hydrogen flowing at a rate of approximately 40 sccm (for a catalyst charge ranging from approximately 0.5 to 2.5 gms total), the temperature of the catalyst beds was increased from 80° F. to reaction temperature (either 900° F., 950° F. or 1000° F.) over a period of at least six hours.

The reactor system was held at reaction temperature with hydrogen for at least two hours.

The catalyst was presulfided by flowing a stream of 1 vol % $H_2S$ in hydrogen over the bed. The time of exposure to the sulfide feed was determined by the amount of catalyst charge. Approximately 1.5 moles of sulfur were fed per mole of Pt present. The off-gas was monitored to check for sulfur breakthrough.

Following sulfiding, the feed was switched back to pure hydrogen for approximately dehydrogenation minutes.

The feed was switched to pure normal butane. The system was allowed to equilibrate for a minimum of two hours prior to gas analysis.

Feed and product analysis were determined using a gas chromatograph equipped with an FID. In this way, complete hydrocarbon analysis was obtained; however, no hydrogen is detected in this manner.

Catalyst properties were monitored with time for a minimum of 70 hours.

Figure 3:
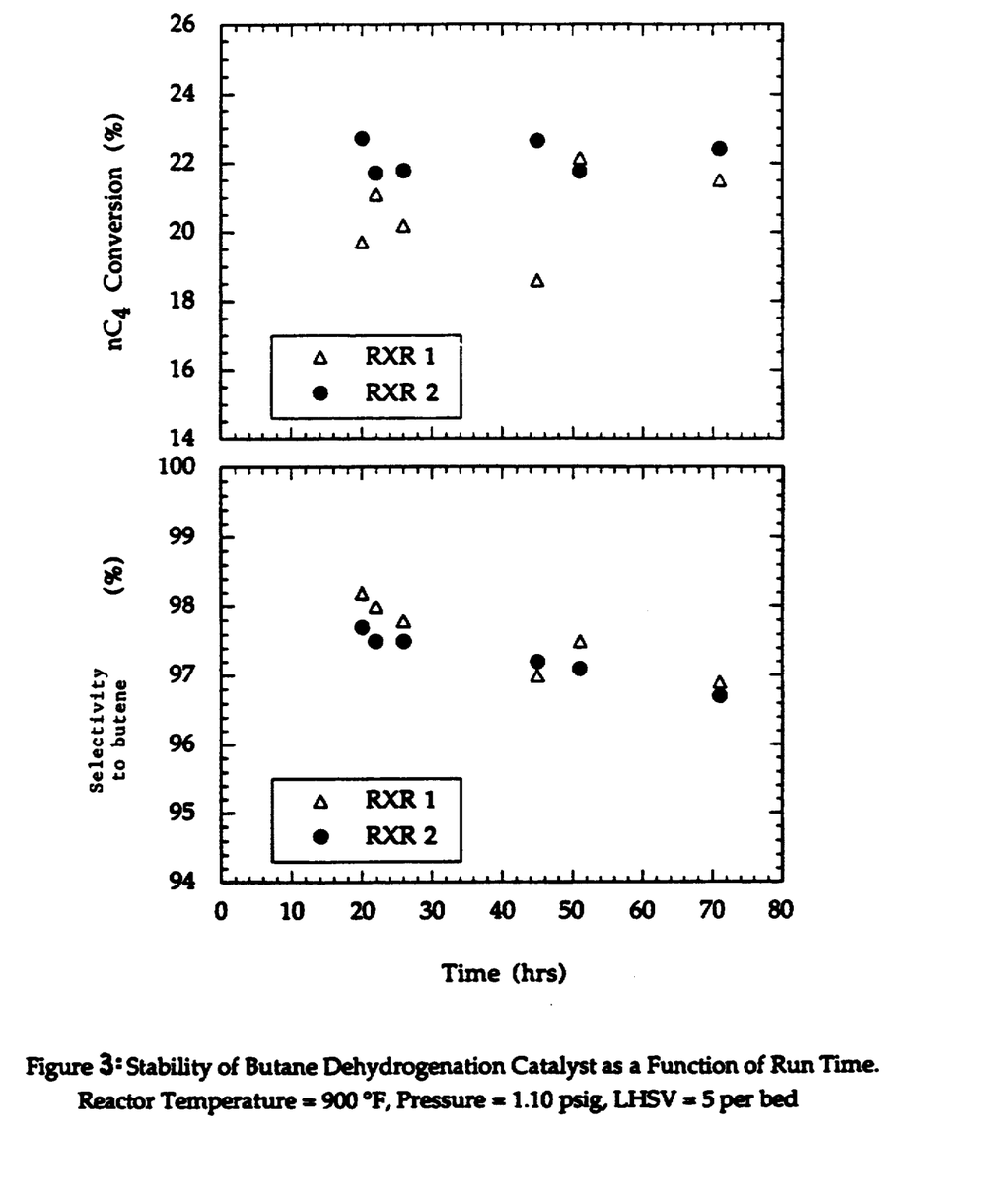
FIG. 3 shows two graphs, one showing time versus butane conversion and the other time versus selectivity which demonstrate the stability of a butane dehydrogenation catalyst as a function of time.

Results from this testing are presented in Table 10 below and a representative stability test shown in FIG. 3. All tests were completed with a feed pressure of 1.1 to 1.2 psig and a product pressure of 1.0 to 1.1 psig. The properties of the catalyst were found to be extremely stable with time and near equilibrium conversion was consistently achieved. As the temperature of the reactors was increased from 900° F. to 1000° F., at a constant LHSV of 5, the conversion of the catalyst increased from 22% to 38%, with a concurrent decrease in the selectivity of the catalyst for butenes.

TABLE 10

| | | n-butane Conversion | | Selectivity | |
|---|---|---|---|---|---|
| Catalyst Performance in Standard Reactor Time on Line = 60 hours Feed Pressure = 1.10 ± 0.10 psig | | | | | |
| Temperature (°F.) | LHSV per bed | Bed 1 | Bed 2 | Bed 1 | Bed 2 |
| 908 | 2 | 24.6 | 26.3 | 96.6 | 95.7 |
| 900 | 5 | 21.1 | 21.8 | 97.5 | 97.1 |
| 898 | 10 | 14.7 | 16.2 | 95.9 | 95.5 |
| 900 | 5 | 21.1 | 21.8 | 97.5 | 97.1 |
| 950 | 5 | 31.7 | 31.9 | 91.7 | 89.7 |
| 1000 | 5 | 33.4 | 37.7 | 85.2 | 82.2 |

In general, the following trends were observed:

Increasing temperature increases conversion but decreases selectivity.

Increasing the space velocity of the system causes a moderate decrease in conversion and has very limited impact on the selectivity of the system. A space velocity of 5 per bed is sufficient to achieve near equilibrium conversion at the temperatures studied.

The properties of the catalyst may show a drift in the first day of operation, but following this point, the levels of conversion and selectivity do not change by more than 1% over the remainder of the test period.

EXAMPLE 4

Dehydrogenation Using Membrane

Having determined the properties of the catalyst of Example 3 as a function of residence time, temperature and pressure, it was possible to examine the ability of a membrane to alter these results. For these tests, a 6FDA-IPDA polymer-ceramic membrane was used while the following conditions were maintained.

| Reactor Conditions: | Membrane Conditions |
|---|---|
| Temperature = 900 ± 2° F. | Membrane Temp = 572 ± 2° F. |
| LHSV = 5 per bed, or 2.5 overall | Membrane Area = 1.95 in² |
| Feed Pressure = 1.10 ± 0.10 psig | Polymer Thickness ≈ 13000 Å |
| Product Pressure = 1.05 ± 0.05 psig | Permeate Pressure < 10 torr |

Utilizing these conditions, a run was completed which lasted over 70 hours. The conversion achieved in product from the second reactor increased from 24% to 32% with the addition of a membrane separator. The properties of the system were stable with time, for the period tested, and the overall selectivity of the system does not appear to be adversely affected by the removal of hydrogen from the second bed. The overall selectivity was about 94% both before and after the addition of the interstage membrane separator.

EXAMPLE 5

Dehydrogenation Using Membrane

Equal volumes of the fresh catalyst of Example 3 were placed in two separate reactors. The catalyst was tested for n-butane dehydrogenation as in Example 4. In this case, the LHSV was set at 5 per bed, or 2.5 overall. Both reactors were maintained at 482° C. (900° F.). The catalyst was presulfided by passing a stream of 1 vol % $H_2S$ in hydrogen over the catalyst at 482° C. The flow of this stream was controlled to provide approximately 2 moles of sulfur per mole of Pt. Following this period the n-butane dehydrogenation capacity of the reactor system was measured at 482° C. and 1.1 psig feed pressure. In this configuration, the n-butane conversion was approximately 22.4% with a selectivity to n-butenes of about 96% to 97%. Following this, a 6FDA-IPDA-ceramic composite membrane sized for complete removal of the hydrogen was installed between the two reactors. The effluent of the first bed was passed over the surface of the membrane where hydrogen was removed due to a partial pressure difference in the two streams. The permeate of the membrane was maintained at less than 10 torr total pressure via a vacuum pump. In this configuration, the conversion achieved in the second reactor increased to about 32.5% while the selectivity to n-butenes remained constant at about 96% to 97%. The flow rate of hydrocarbons from the second reactor with the membrane in place was 100±2% of that measured in the absence of the membrane.

What is claimed is:

1. A process for dehydrogenating a light paraffin hydrocarbon feed, said process comprising:
   A. contacting said feed under catalytic dehydrogenation conditions with a dehydrogenation catalyst;
   B. contacting the effluent from the dehydrogenation reaction of step A with a polymer-porous solid composite membrane capable of separating hydrogen from said effluent, thereby separating said effluent into components comprising (1) hydrogen and (2) a mixture comprising paraffin and olefin.

2. The process of claim 1 further comprising:
   C. contacting said mixture of paraffin and olefin with a dehydrogenation catalyst under dehydrogenation conditions.

3. A process for dehydrogenating a light paraffinic hydrocarbon feed in a reaction zone which may be subjected to periodic exposure to more than 100 ppb sulfur, which process comprises:
   A. contacting the feed under catalytic dehydrogenation conditions with a catalyst comprising:
      (a) a noble metal;
      (b) an intermediate pore size zeolite having a silica to alumina mole ratio of about 30 or greater; and
      (c) an alkali content wherein the alkali to aluminum ratio in the zeolite is between about 1 and about 5 on a molar basis;
   B. contacting the effluent from the dehydrogenation reaction of step A with a polymer-porous solid composite membrane capable of separating hydrogen from said effluent, thereby separating said effluent into components comprising (1) hydrogen and (2) a mixture comprising paraffin and olefin.

4. The process of claim 3 further comprising:
   C. contacting said mixture of paraffin and olefin with a dehydrogenation catalyst under dehydrogenation conditions.

5. The process of claim 1, 2, 3 or 4 wherein the polymer used for the polymer-porous solid composite is selected from the group consisting of fluorinated dianhydride diamines, fluorinated polycarbonates and fluorinated polysulfones.

6. The process of claim 5 wherein the fluorinated dianhydride-diamine is 4,4'-[2,2,2-trifluoro-1-(trifluoromethyl)ethylidene]bis-1,3-isobenzofurandione, isopropylideneaniline or 4,4'-2,2,2-trifluoro-1-(trifluoromethyl)ethylidene]bis-1,3-isobenzofurandione, methyleneaniline.

7. The process of claim 5 wherein the fluorinated polycarbonate is tetramethylhexafluorobishphenol-A polycarbonate.

8. The process of claim 5 wherein the fluorinated polysulfone is tetramethylhexafluoropolysulfone.

9. The process of claim 1, 2, 3, or 4 wherein the porous solid is a ceramic.

10. The process of claim 9 wherein the ceramic has an average surface pore diameter of about 200 Å or less.

* * * * *

UNITED STATES PATENT AND TRADEMARK OFFICE
CERTIFICATE OF CORRECTION

PATENT NO. : 5,430,218

DATED : July 4, 1995

INVENTOR(S) : Stephen J. Miller ET AL

It is certified that error appears in the above-identified patent and that said Letters Patent is hereby corrected as shown below:

Claim 5, Col. 28, line 22  "dianhydride diamines" should read --dianhydride-diamines--

Claim 6, Col. 28, line 27  "2,2,2-trifluoro-1-" should read --[2,2,2-trifluoro-1- --

Signed and Sealed this

Twelfth Day of September, 1995

Attest:

BRUCE LEHMAN

Attesting Officer    Commissioner of Patents and Trademarks